United States Patent
Schnitzspan et al.

(10) Patent No.: US 9,877,814 B2
(45) Date of Patent: Jan. 30, 2018

(54) METHODS, APPARATUSES, COMPUTER PROGRAMS, AND SYSTEMS FOR CREATING A CUSTOM DENTAL PROSTHESIS USING A CAD/CAM SYSTEM

(71) Applicant: Sirona Dental Systems GmbH, Bensheim (DE)

(72) Inventors: Paul Schnitzspan, Frankfurt (DE); Thorsten Jordan, Pfungstadt (DE)

(73) Assignee: Sirona Dental Systems GmbH, Bensheim (DE)

( * ) Notice: Subject to any disclaimer, the term of this patent is extended or adjusted under 35 U.S.C. 154(b) by 168 days.

(21) Appl. No.: 14/701,956

(22) Filed: May 1, 2015

(65) Prior Publication Data
US 2016/0317260 A1   Nov. 3, 2016

(51) Int. Cl.
| A61C 13/10 | (2006.01) |
| A61C 13/00 | (2006.01) |
| A61C 13/01 | (2006.01) |
| A61C 13/08 | (2006.01) |

(52) U.S. Cl.
CPC ...... A61C 13/1003 (2013.01); A61C 13/0004 (2013.01); A61C 13/0006 (2013.01); A61C 13/01 (2013.01); A61C 13/082 (2013.01)

(58) Field of Classification Search
USPC ........................................................ 433/171
See application file for complete search history.

(56) References Cited

U.S. PATENT DOCUMENTS

| 2,469,822 A * | 5/1949 | Giese | A61C 13/10 264/16 |
| 2,596,941 A * | 5/1952 | Quintella | A61C 13/00 433/171 |
| 2,641,802 A * | 6/1953 | Grant | A61C 13/10 264/19 |
| 3,644,996 A * | 2/1972 | Weinkle | A61C 13/1013 433/171 |
| 3,838,513 A * | 10/1974 | Katz | A61C 13/0001 433/171 |
| 3,846,911 A * | 11/1974 | Wichner | A61C 13/00 433/171 |
| 4,337,042 A * | 6/1982 | von Nostitz | A61C 13/1013 433/171 |
| 4,370,133 A * | 1/1983 | Stempel | A61C 13/0001 433/171 |
| 4,470,815 A * | 9/1984 | Hazar | A61C 13/00 264/18 |
| 4,514,173 A * | 4/1985 | Re | A61C 13/225 433/178 |
| 4,583,947 A * | 4/1986 | Hazar | A61C 13/00 264/18 |
| 4,583,949 A * | 4/1986 | Heartness | A61C 13/25 433/185 |

(Continued)

*Primary Examiner* — Kennedy Schaetzle
(74) *Attorney, Agent, or Firm* — Fitzpatrick, Cella, Harper & Scinto (57) ABSTRACT

Preparation of a dental prosthesis that includes a gingiva part having retention holes for seating of manufactured teeth, with the retention holes being enlarged relative to the manufactured teeth. Wax in the enlarged retention holes permits adjustments in positioning of the manufactured teeth, and a helper structure preserves this positioning when the wax is removed and a curable gingiva material is filled into the retention holes. Aspects described herein include digital and/or automatic design of the dental prosthesis and its constituent pieces, as well as automated fabrication thereof in whole or in part, such as in a dental CAD/CAM system.

34 Claims, 7 Drawing Sheets

(56) References Cited

U.S. PATENT DOCUMENTS

| | | | | |
|---|---|---|---|---|
| 4,654,006 A * | 3/1987 | Kusano | ................... | A61C 13/04 264/17 |
| 4,744,758 A * | 5/1988 | Harrison | ............ | A61C 13/2653 433/181 |
| 5,527,182 A * | 6/1996 | Willoughby | ......... | A61C 8/0001 433/172 |
| 6,056,547 A * | 5/2000 | Names | ................. | A61C 8/0001 433/173 |
| 7,670,516 B2 * | 3/2010 | Rusler | ................ | A61C 13/0025 264/16 |
| 7,758,346 B1 * | 7/2010 | Letcher | ................ | A61C 8/0048 433/172 |
| 8,545,224 B2 * | 10/2013 | Baptiste | ............. | A61C 13/1016 433/171 |
| 8,875,398 B2 * | 11/2014 | Balshi | ................... | A61C 8/0048 29/896.1 |
| 2002/0064759 A1 * | 5/2002 | Durbin | ..................... | A61C 9/00 433/213 |
| 2002/0162642 A1 * | 11/2002 | Walker, Sr. | ............... | B22C 9/04 164/516 |
| 2004/0133293 A1 * | 7/2004 | Durbin | ............... | A61C 13/0004 700/98 |
| 2010/0076581 A1 * | 3/2010 | Violante | ............ | A61C 13/0004 700/98 |
| 2010/0183998 A1 * | 7/2010 | Poirier | ................. | A61C 8/0048 433/72 |
| 2012/0291284 A1 * | 11/2012 | Warden | .............. | A61C 13/0004 29/896.1 |
| 2016/0317260 A1 * | 11/2016 | Schnitzspan | ....... | A61C 13/0004 |

* cited by examiner

METHODS, APPARATUSES, COMPUTER PROGRAMS, AND SYSTEMS FOR CREATING A CUSTOM DENTAL PROSTHESIS USING A CAD/CAM SYSTEM

BACKGROUND

Field

The present disclosure relates generally to dental restorations, in particular, to the use of a CAD/CAM system to produce a dental prosthesis.

Background

Restoring or repairing one or more of a patient's teeth often involves the preparation and attachment of a dental prosthesis, such as a denture. Dentures are constructed to replace missing teeth and are supported by the surrounding soft and hard tissues of the oral cavity. Dentures are generally removable and can comprise either partial or complete dentures. Partial dentures are prepared for patients who are missing some of their teeth on a particular arch (i.e., the maxillary (upper) or mandibular (lower) arch), while complete dentures are prepared for patients who are missing all of their teeth in a single arch or in both arches (i.e., a toothless patient).

Preparation of a dental prosthesis, such as a denture, is preceded by making an impression of the dental patient's oral cavity in the area of the restoration site. This impression should accurately reflect the physical features of the dental patient's oral cavity. An accurate impression can yield a well-fitting dental prosthesis that is secure and comfortable in the patient's mouth, and that is long-lasting and aesthetically pleasing. An ill-fitting dental prosthesis, on the other hand, can increase the patient's risk of infection or disease, and cause shifting in the prepared prosthesis.

Obtaining a well-fitting dental prosthesis, such as a denture, is not an insignificant task. For example, during casting and curing of a final denture, errors, such as transference errors, can occur when transferring the features of the patient's oral cavity and/or the accurate positioning of denture teeth to the final cast denture. Such transference errors occur due to the imprecision of the production process. Accordingly, several iterations of test fitting (e.g., check biting) the denture with the patient and thereafter, adapting of the denture via various finishing steps by a technician may be required to create a well-fitting prosthesis. In addition, a final cast denture may result in bubbles within the casting that reduce the aesthetics and the stability of the final dental prosthesis. Moreover, in certain situations, an entirely new dental prosthesis may be required to be recast in the case of an ill-fitting prosthesis that cannot be readily adapted for the patient's mouth by the dentist and/or technician.

SUMMARY

In one aspect, the problems associated with preparing a well-fitting dental prosthesis can be addressed by creating a custom dental prosthesis using a computer-aided design/computer-assisted manufacturing (CAD/CAM) system, the dental prosthesis being easily adaptable to a dental patient's oral cavity. According to aspects described herein, for reducing transference errors related to the features of the patient's oral cavity and/or the positioning of manufactured teeth in a dental prosthesis, the dental prosthesis is prepared with a gingiva part having enlarged retention holes for receiving the manufactured teeth, thus providing improved flexibility in seating of the manufactured teeth. After bite adjustment in which wax is used for positioning the manufactured teeth within the enlarged retention holes, the wax may be replaced with curable gingiva material, to fix the position of the manufactured teeth more permanently.

In further aspects, a dental prosthesis created via a CAD/CAM system can be fabricated into a final prosthesis base by, for example, milling a final-strength, gingiva colored material using the CAD/CAM system, thus, potentially removing the need for casting of the final prosthesis base and the problems associated with such casting. In one aspect, enlarged retention holes are created within the final prosthesis base to compensate for any errors in transferring the features of the patient's oral cavity and/or the positioning of manufactured teeth to the final prosthesis base. The enlarged retention holes are enlarged with respect to manufactured denture teeth. In another aspect, the final dental prosthesis can be manually adapted within the patient's mouth using the enlarged retention holes that are filled with both denture teeth and a millable and moldable wax. In yet another aspect, the final dental prosthesis is completed by filling the enlarged retention holes with a curable liquid gingiva material and denture teeth that have been adjusted for the specific features of a patient's oral cavity.

One embodiment described herein relates to a fabricated gingiva part of a dental prosthesis. The gingiva part comprises a gingiva base fabricated out of a final strength, gingiva colored material, and a plurality of retention holes in the gingiva base for seating manufactured teeth, wherein the retention holes are enlarged relative to the manufactured teeth. In one aspect, the enlarged retention holes of the fabricated gingiva part are filled with a wax and at least one manufactured tooth. In another aspect, the enlarged retention holes of the fabricated gingiva part are filled with a curable liquid gingiva material and at least one manufactured tooth.

Another embodiment described herein relates to preparation of a dental prosthesis. A gingiva part is digitally designed together with at least one manufactured tooth of a dental prosthesis, the gingiva part including retention holes for seating manufactured teeth, and the retention holes being enlarged relative to the manufactured teeth. The gingiva part of the dental prosthesis is fabricated out of a final strength, gingiva colored base to create a fabricated gingiva part, the fabricated gingiva part including the enlarged retention holes. In one aspect, the gingiva part and the at least one manufactured tooth is digitally designed using a computer-aided design (CAD) system, and the gingiva part of the dental prosthesis is fabricated using a computer-assisted manufacturing (CAM) milling system. In another aspect, the enlarged retention holes of the fabricated gingiva part are each filled with a wax, a portion of the wax is removed from each of the enlarged retention holes, such that the removed wax comprises a negative part of a manufactured tooth to be seated in each of the enlarged retention holes, the manufactured tooth is mounted to each of the enlarged retention holes, and a position of at least one of the manufactured teeth mounted to the enlarged retention holes is adjusted. In yet another aspect, a helper structure is attached to the position-adjusted manufactured teeth so as to preserve a positioning thereof relative to the gingiva part, and any wax remaining within each of the enlarged retention holes is removed. In another aspect, each of the retention holes is filled with a liquid gingiva material, and the liquid gingiva material is cured to complete the final dental prosthesis.

Another embodiment described herein relates to a computer for preparing a dental prosthesis. The computer comprises at least one processor operable to digitally design a gingiva part and at least one manufactured tooth of the dental prosthesis. The gingiva part includes retention holes for seating manufactured teeth, the retention holes being enlarged relative to the manufactured teeth, and the enlarged retention holes being automatically generated by the processor. In one aspect, the processor is included in a dental CAD/CAM device. In another aspect, a milling system is provided that is configured to fabricate the gingiva part out of a final strength, gingiva colored base based on the digital design, the gingiva part including the enlarged retention holes. In yet another aspect, the processor is further operable to adjust a size, a position, and/or a location of the enlarged retention holes, such that the adjustment is based on stored information that includes (i) measurements related to adjacent teeth, (ii) measurements related to sizing of an inner boundary of the enlarged retention holes, and/or (iii) measurements related to sizing of an outer boundary of the enlarged retention holes.

Another embodiment described herein relates to a sequence of instructions which, when executed by a computer system, cause the computer system to digitally design a gingiva part and at least one manufactured tooth of a dental prosthesis. The gingiva part includes retention holes for seating manufactured teeth, the retention holes being enlarged relative to the manufactured teeth, and the enlarged retention holes being automatically generated by the computer system. In one aspect, the instructions further cause the computer system to fabricate the gingiva part of the dental prosthesis based on the digital design, the gingiva part including the enlarged retention holes. In another aspect, the instructions further cause the computer system to adjust a size, a position, and/or a location of the enlarged retention holes, such that the adjustment is based on stored information that includes (i) measurements related to adjacent teeth, (ii) measurements related to sizing of an inner boundary of the enlarged retention holes, and/or (iii) measurements related to sizing of an outer boundary of the enlarged retention holes.

The various embodiments described herein can be useful for compensating for errors in the transmission of the features of the patient's oral cavity and/or the accurate positioning of denture teeth to a final dental prosthesis, which thereby improves the aesthetics, stability, and ease of production of the final dental prosthesis. The various embodiments described herein can also be useful for producing a final prosthesis base without casting the base in a conventional manner, which thereby reduces the complicated steps of preparing and finishing the prosthesis base, and further removes the issue of bubbles in the cast base that reduce the aesthetics and the stability of the final dental prosthesis. As understood by one of ordinary skill in the art, the various embodiments described herein can be especially advantageous in preparing a well-fitting dental prosthesis for a toothless dental patient given that a complete custom-made denture can be prepared that compensates for errors in the transmission of the features of the patient's oral cavity and/or the accurate positioning of denture teeth.

Further features and advantages, as well as the structure and operation of various embodiments herein, are described in detail below with reference to the accompanying drawings.

BRIEF DESCRIPTION OF THE DRAWINGS

The teachings claimed and/or described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

Different ones of the Figures may have at least some reference numerals that are the same in order to identify the same components, although a detailed description of each such component may not be provided below with respect to each Figure.

DETAILED DESCRIPTION

In accordance with example aspects described herein, methods, systems, apparatuses, and computer programs are provided for creating a dental prosthesis using a CAD/CAM system.

A restoration site is generally an area of a patient's oral cavity in which one or more teeth can be restored, repaired, or replaced by a dental prosthesis. A restoration site may (or may not) include areas in which a tooth or teeth are missing, such as when a patient has lost a tooth or a tooth has been removed during preparation for a dental impression. The restoration site can include teeth adjacent to those that will be directly affected by a dental prosthesis, although it need not include such teeth. A restoration site can include teeth (hard tissue) local to the site, as well as gingiva (soft tissue), and any other portion of the oral cavity local to the site, such as the alveolar bone. The restoration site may (or may not) further include one or more dental implants that interface with the bone of the jaw or skull of a dental patient to support a dental prosthesis. The one or more dental implants must first be surgically placed within the dental patient's mouth in order to thereafter attach the dental prosthesis to the dental implant.

Dental prosthesis generally are, for example, artificial or man-made structures that replace part or all of a patient's dentition at a restoration site. Some examples of dental prosthesis include, without limitation, dental restorations, such as dentures. A dental prosthesis can be permanent or temporary, and its use may be clinically indicated or elected by a patient.

Figure 1A:
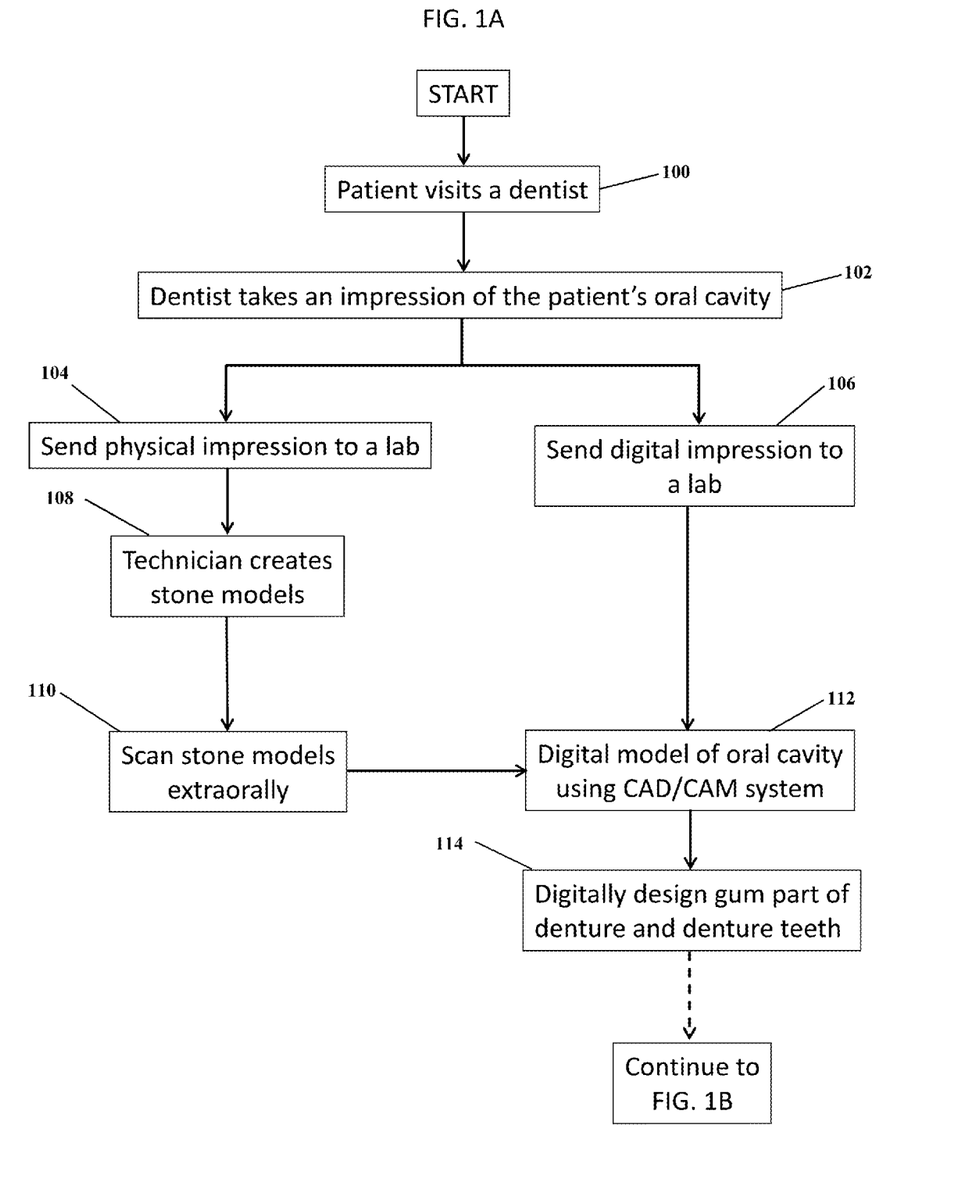
FIG. 1A is a flow diagram of an example procedure for creating a dental prosthesis, in accordance with an example embodiment herein.
Figure 1B:
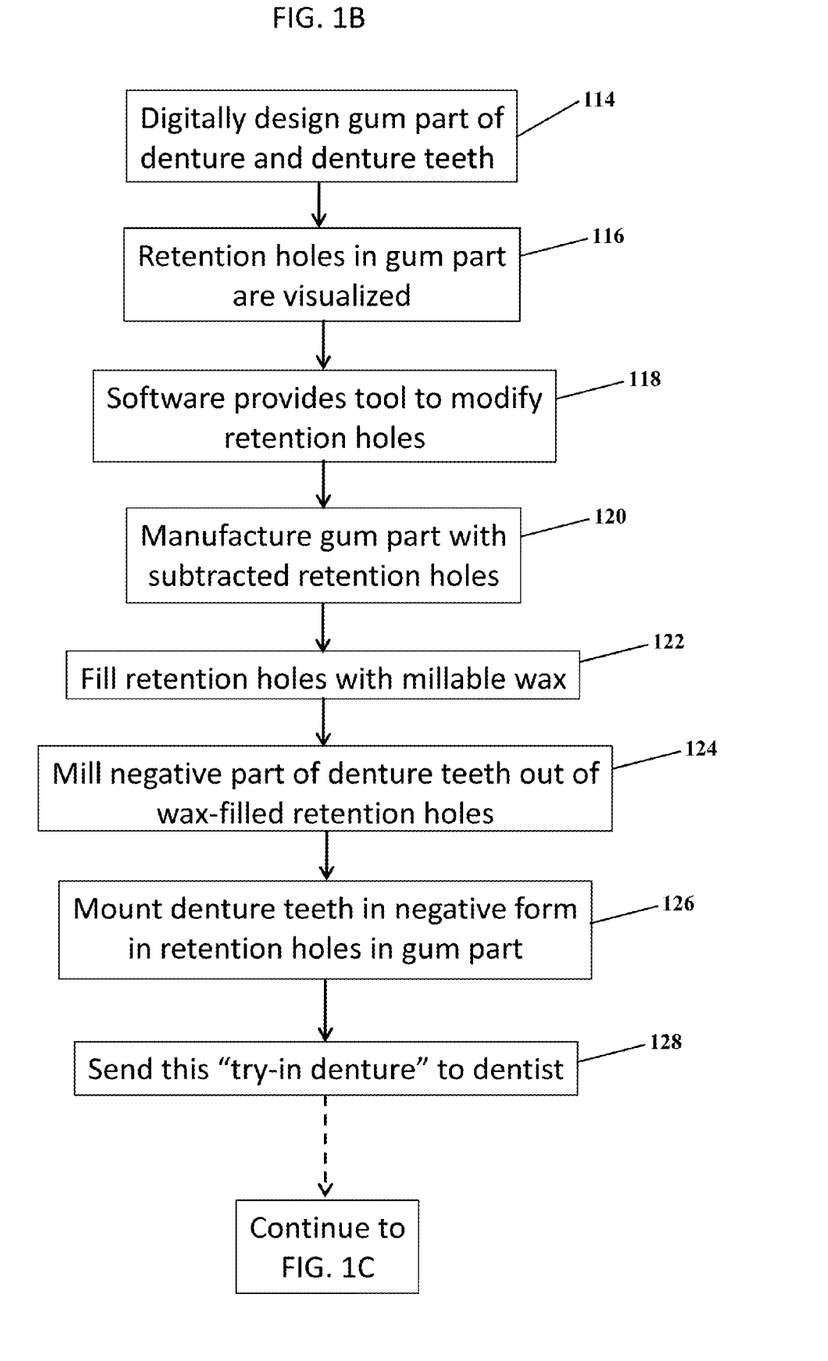
FIG. 1B is a flow diagram of an example procedure for creating a dental prosthesis, in accordance with FIG. 1A.
Figure 1C:
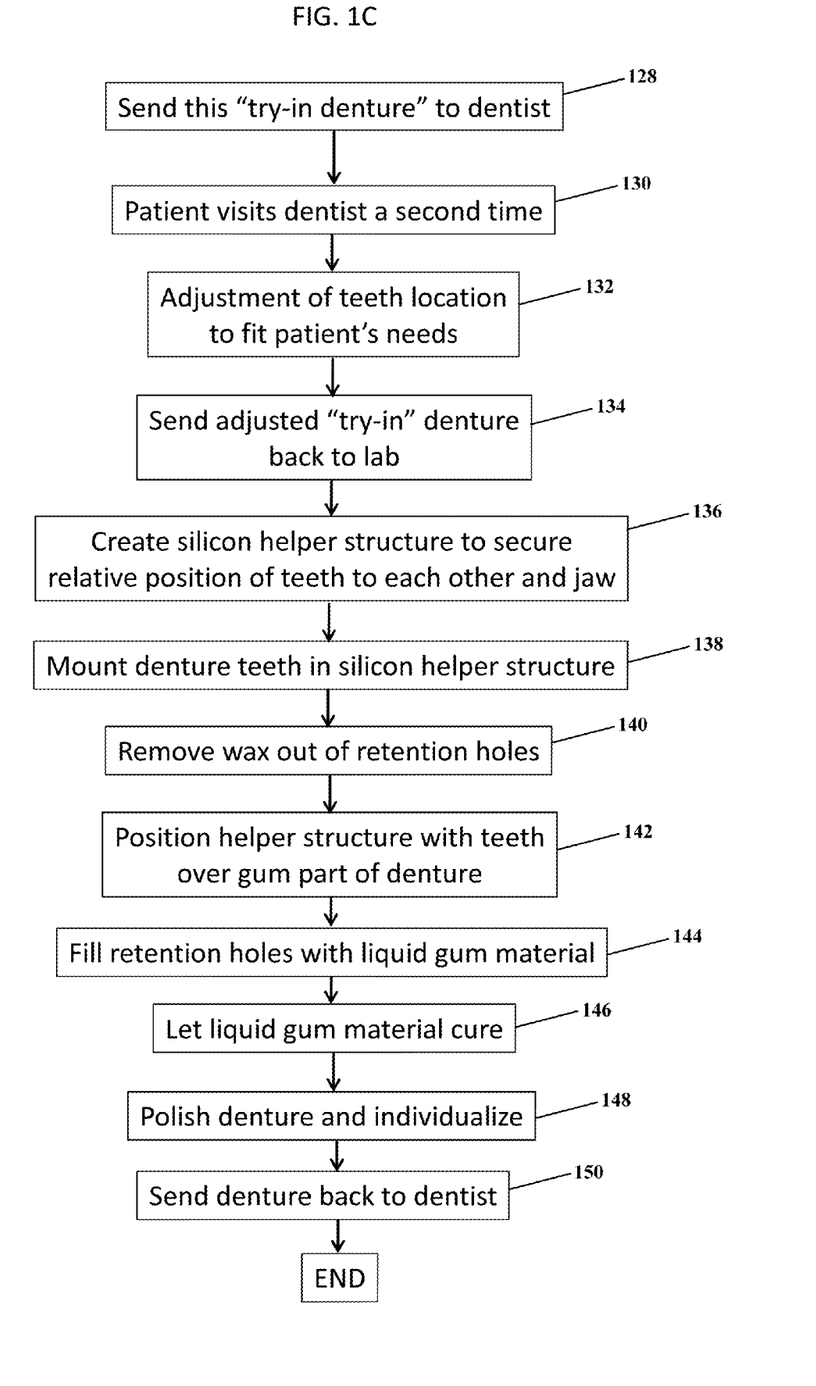
FIG. 1C is a flow diagram of an example procedure for creating a dental prosthesis, in accordance with FIGS. 1A and 1B.

FIGS. 1A-1C illustrate a flow diagram of an example procedure for creating a dental prosthesis configured in accordance with an example embodiment herein. Briefly, according to FIGS. 1A-1C, a dental prosthesis is prepared in which a gingiva part of the dental prosthesis is digitally designed together with at least one manufactured tooth of the dental prosthesis, the gingiva part including retention holes for seating manufactured teeth, and the retention holes being enlarged relative to the manufactured teeth. The gingiva part of the dental prosthesis is fabricated out of a final strength, gingiva colored base to create a fabricated gingiva part, the fabricated gingiva part including the enlarged retention holes. The gingiva part and the at least one manufactured tooth is digitally designed using a computer-aided design (CAD) system, and the gingiva part of the dental prosthesis is fabricated using a computer-assisted manufacturing (CAM) milling system. In one aspect, the enlarged retention holes of the fabricated gingiva part are each filled with a wax, a portion of the wax is removed from each of the enlarged retention holes, such that the removed wax comprises a negative part of a manufactured tooth to be seated in each of the enlarged retention holes, the manufactured tooth is mounted to each of the enlarged retention holes, and a position of at least one of the manufactured teeth mounted to the enlarged retention holes is adjusted. In another aspect, a helper structure is attached to the position-adjusted manufactured teeth so as to preserve a positioning thereof relative to the gingiva part, and any wax remaining within each of the enlarged retention holes is removed. In yet another aspect, each of the retention holes is filled with a liquid gingiva material, and the liquid gingiva material is cured to complete the final dental prosthesis.

In more detail, as shown in FIG. 1A, the example procedure begins at step 100 in which a dental patient visits the dentist. In one example embodiment, step 100 occurs after one or more teeth have been surgically removed from the patient's mouth. Thereafter, at step 102, the dentist will take an impression of the patient's oral cavity. In one example embodiment, the impression can be a physical impression. This provides an imprint of the restoration site, which often is made using an intraoral mold, and from which the dental prosthesis, e.g., denture, is produced. In the case of the dentist preparing a physical impression of the patient's oral cavity, the physical impression is thereafter sent to a lab at step 104, where a technician will create a stone model(s) using the physical impression at step 108. Thereafter, at step 110, the stone model(s) will be extraorally scanned using an imaging system, such as, for example, an optical digital camera or any other type of image acquisition device that is capable of generating a three-dimensional model of a real geometry. The scanning of the stone model(s) at step 110 will create a scanned image of the stone model, which can be used to produce a digital model of the oral cavity at step 112 using a CAD/CAM system.

Alternatively, in another example embodiment, the impression of the patient's oral cavity taken at step 102 can be a digital impression that is produced using an imaging system, such as, for example, an optical digital camera or another type of image acquisition device, as discussed above. In various examples, an optical digital camera can perform imaging procedures and generate image data intra-orally (e.g., image acquisition occurring inside of a patient's mouth) and/or extraorally (e.g., image acquisition occurring outside of a patient's mouth). Also in various examples, an optical digital camera can perform image acquisition either automatically, e.g., without user intervention, or manually in response to operator commands. In one embodiment, the digital impression is created by conducting an intra-oral scan of the patient's oral cavity. The intra-oral scan can be conducted by placing an optical digital camera inside the patient's mouth, and capturing images of the patient's specific oral cavity. Using various patterns of light, it is possible to scan height variations of the features of the oral cavity and to generate three-dimensional data from the scans. Alternatively, a laser based scanner could be used to measure distances and/or heights of features of the patient's oral cavity over a specific area.

Once the digital impression is captured of the patient's oral cavity, such as, for example, via the intra-oral scan, the digital impression of the patient's oral cavity (as opposed to the physical impression discussed above) will be sent to a lab in step 106. This digital impression of the patient's oral cavity can thereafter be used to create a digital model of the patient's oral cavity using a CAD/CAM system at step 112. The digital model created at step 112 using the CAD/CAM system will be substantially similar, if not identical, to that prepared above in which a physical impression is first taken of the patient's oral cavity.

In one example embodiment, once the digital model of the patient's oral cavity is created in step 112 using a CAD/CAM system, a technician digitally designs the gum or gingiva part of a dental prosthesis, e.g., denture, along with at least one denture tooth using the CAD/CAM system at step 114. In one embodiment, the digitally designed denture teeth comprise digital representations of one or more premanufactured teeth, such as those available from VITA Zahnfabrik, Bad Sackingen, Germany, VITA North America, Yorba Linda, Calif., or Heraeus Kulzer North America, South Bend, Ind., in which the specifications and geometry of the various premanufactured teeth can be stored within a database of the CAD/CAM system. In another embodiment, the digitally designed denture teeth comprise one or more computer-generated teeth that are generated using a computer program and/or algorithm. In yet another embodiment, the digitally designed teeth are selected from a computer database designed as a source for CAM-produced teeth, such as, for example, one or more biogeneric teeth that are contained within a database of the CAD/CAM system, such as those described in U.S. Pat. No. 8,727,776, which is incorporated by reference in its entirety, as if set forth fully herein. In another embodiment, the CAD/CAM system includes software that automatically selects denture teeth, such as the premanufactured teeth and/or the biogeneric teeth of the databases discussed above, for the digital design, along with the relative positioning of the denture teeth within the gingiva part of the dental prosthesis.

Figure 2A:
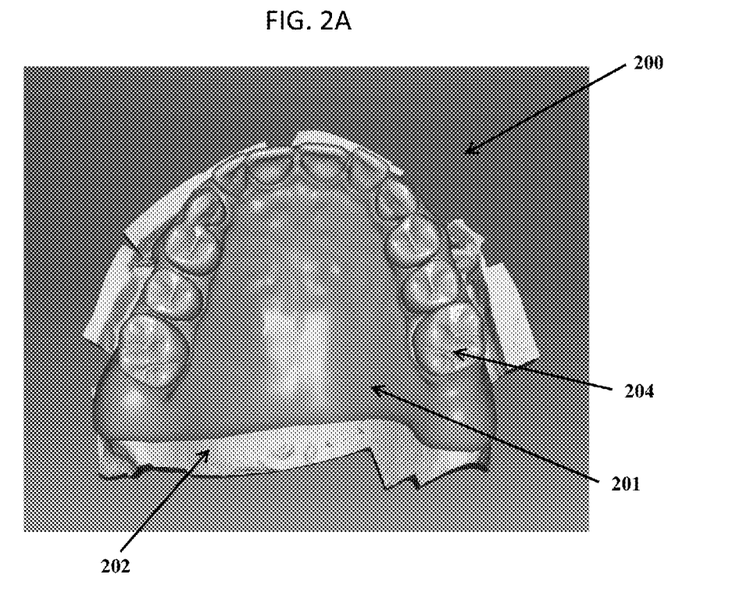
FIG. 2A is a view for illustrating an image of the dental prosthesis configured in accordance with an example embodiment herein.
Figure 2B:
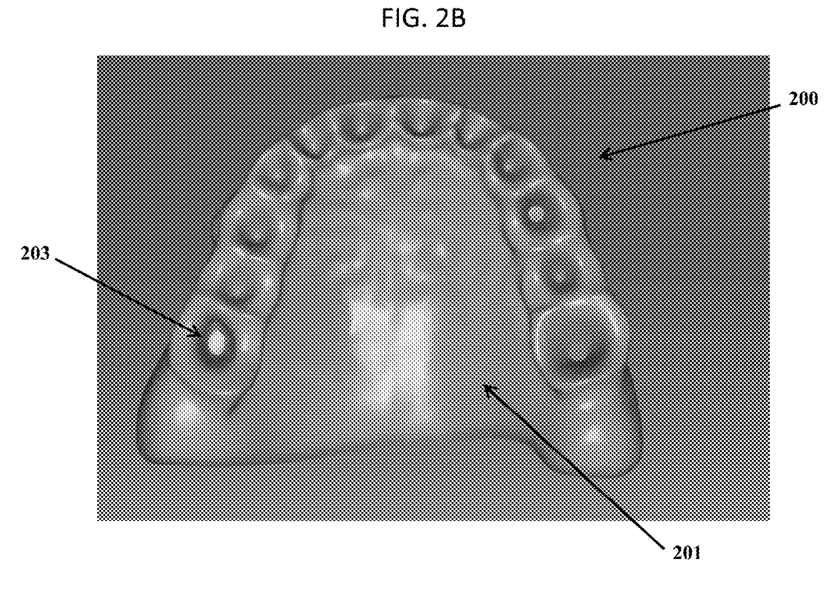
FIG. 2B is a view for illustrating an image of retention holes of the dental prosthesis configured in accordance with FIG. 2A.

Thereafter, at step 116, enlarged retention holes 203 are created and visualized in the digitally designed gum or gingiva part of the dental prosthesis prepared in step 114 using the CAD/CAM system (see, e.g., FIG. 2B). The enlarged retention holes 203 are enlarged relative to the denture teeth or manufactured teeth, discussed above. In one embodiment, the CAD/CAM system will include software that automatically proposes the locations and sizes of the enlarged retention holes 203, such that the locations and sizes of the retention holes are computed relative to the denture teeth. In particular, the software can compute the sizing and geometry of each retention hole in relation to the sizing and geometry of each respective denture tooth, so that the respective denture tooth will be capable of being rotated and moved within the respective retention hole by a certain amount that is generally needed to adjust the tooth relative to the specific features of patient's oral cavity. In another embodiment, the software further allows for modifying the retention holes 203 created within the digitally designed gingiva part of the dental prosthesis, which will be fully described hereinafter with respect to FIGS. 2A-2D. In particular, the software provides a tool at step 118 for modifying the retention holes 203, which will be more fully described with respect to FIGS. 2A-2D.

Briefly, according to FIGS. 2A-2D, a computer comprising at least one processor operable to digitally design a gingiva part and at least one manufactured tooth of a dental prosthesis is provided. The gingiva part includes retention holes for seating manufactured teeth, the retention holes being enlarged relative to the manufactured teeth, and the enlarged retention holes being automatically generated by the processor. In one aspect, the processor is included in a dental CAD/CAM device. In another aspect, a milling system is provided that is configured to fabricate the gingiva part out of a final strength, gingiva colored base based on the digital design, the gingiva part including the enlarged retention holes. In yet another aspect, the processor is further operable to adjust a size, a position, and/or a location of the enlarged retention holes, such that the adjustment is based on stored information that includes (i) measurements related to adjacent teeth, (ii) measurements related to sizing of an inner boundary of the enlarged retention holes, and/or (iii) measurements related to sizing of an outer boundary of the enlarged retention holes.

In more detail, in one example embodiment, as shown in FIG. 2A, a digital design of a dental prosthesis, i.e., a denture 200, is created in, for example, step 114, as discussed above. In the digital design of the denture 200, a digital image of the stone model 202 is illustrated, as well as the digitally designed gum or gingiva part 201 and denture teeth 204. As shown in FIG. 2B, the digital design of the denture 200 further includes enlarged retention holes 203 that are digitally created by the technician or automatically proposed by software included with the CAD/CAM system, as discussed above with respect to step 116 of FIG. 1B. These enlarged retention holes 203 are of a size to accommodate the denture teeth 204, but are also of a size slighter larger than the denture teeth 204, such that the positioning of the denture teeth can be adjusted to fit the needs of the patient's specific oral cavity, as discussed in more detail below.

Figure 2C:
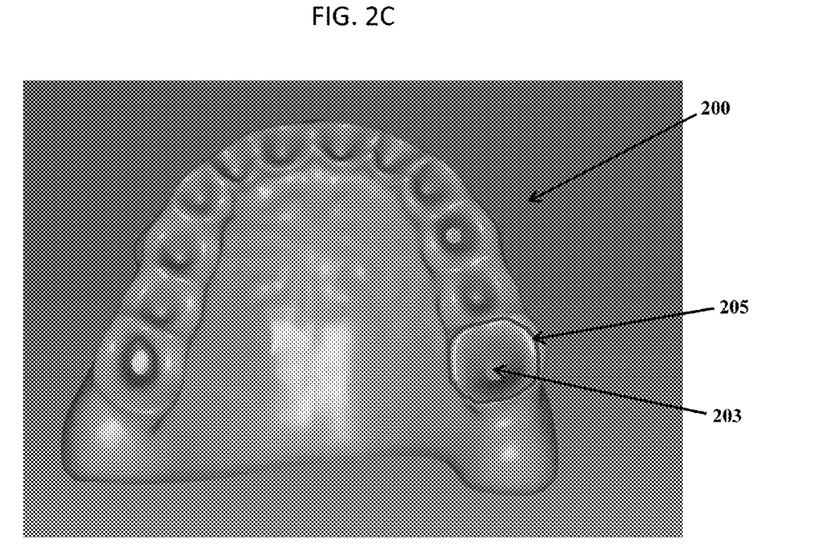
FIGS. 2C and 2D are views for illustrating modification of the retention holes of the dental prosthesis configured in accordance with FIGS. 2A and 2B.
Figure 2D:
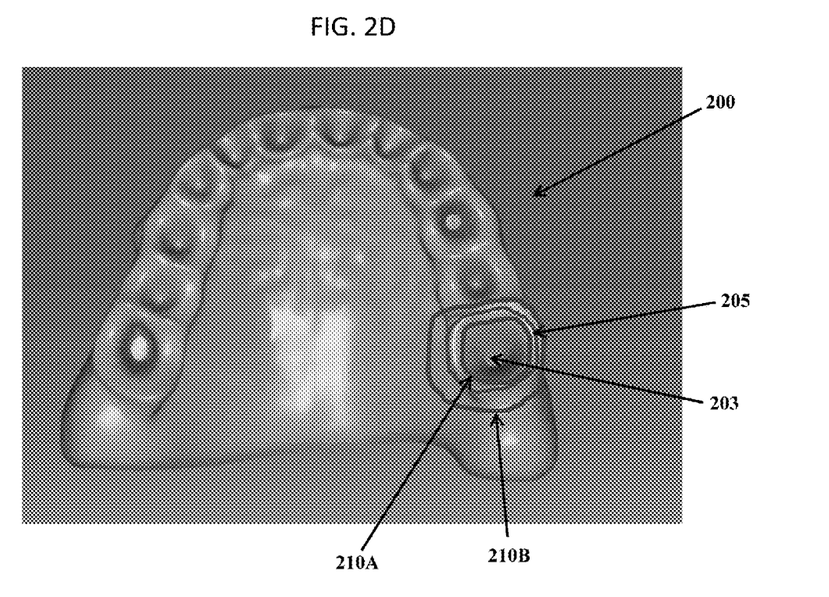

In another example embodiment, as shown in FIG. 2C, the software includes a tool 205 that allows for modifying the location, positioning, and/or sizing of the retention holes 203 in the digital design of the denture 200, as discussed above with respect to step 118 of FIG. 1B. In particular, this tool 205 can be used by the technician to increase or decrease the outer margins of the retention holes 203 by clicking the tool 205 on the specific retention hole 203 with a button of an input unit, such as a mouse, and by moving or rotating the tool 205 and thus, the margin of the retention hole 203, to another location or position by, for example, holding down the button of the input unit until the alternate location or position is selected. In the embodiment of FIG. 2D, the software can further provide highlighted areas 210A, 210B around the proposed location for the retention hole 203 in which the user or technician can effectively increase or decrease the margins of the proposed retention hole 203. The highlighted areas 210A, 210B include an inner boundary 210A and an outer boundary 210B indicating how much the margins of the retention hole 203 can be effectively decreased or increased, respectively. In one example embodiment, the highlighted areas 210A, 210B are preferably of a color that is distinctive from the gingiva part 201 and/or the modification tool 205, such as, for example, a red color. The highlighted areas 210A, 210B are created from various information collected by the system. In one example embodiment, this information includes: (i) measurements related to adjacent teeth 204, ensuring that the margins do not intersect with the adjacent teeth 204, (ii) measurements related to the sizing of the inner boundary 210A of the retention holes 203, such that the retention holes 203 will be large enough to allow for a degree of freedom to adjust the teeth 204 during the initial fitting of the prosthesis with the patient, and/or (iii) measurements related to the sizing of the outer boundary 210B of the retention holes 203, such that the retention holes 203 will be small enough to ensure stability and/or an aesthetic appearance. Accordingly, the highlighted areas 210A, 210B include information related to the positioning and/or sizing of the retention holes 203 to ensure accurate placement on the gingiva part 201 of the digitally designed dental prosthesis.

Once the CAD/CAM system and/or the user is finished with the digital design of the gingiva part 201, the teeth 204, and the enlarged retention holes 203, the digital design of the denture 200 is complete. In one example embodiment, once the digital design of the denture 200 is complete, the gingiva part of the denture with the subtracted retention holes 203 is fabricated at step 120 using either an additive or subtractive manufacturing procedure. One example embodiment of an additive procedure for fabricating the gingiva part of the denture is stereolithography or optical fabrication. Another example embodiment of an additive manufacturing procedure is 3D-printing of plastics and/or wax. However, a person skilled in the relevant art(s) could fabricate the invention using other additive manufacturing procedures, and doing so is within the scope of the invention.

In one example embodiment of a subtractive manufacturing procedure, the CAD/CAM system controls a milling system or milling machine to fabricate the gingiva part of the denture. The gingiva part is fabricated by the milling system out of a final-strength prosthesis base material that is preferably made of a gingiva colored material. In an example embodiment, a milling system includes a milling machine having one or more computer-controlled burrs or other grinding and/or cutting components to mill, cut and/or grind a final-strength prosthesis base material block into the pre-determined shape of the gingiva part of the denture, including the subtracted retention holes 203, based on the CAD/CAM digital model created in steps 114-118 of FIG. 1B, thereby producing a final dental prosthesis base.

The final dental prosthesis base, fabricated by either an additive or subtractive manufacturing procedure, will include the enlarged retention holes, discussed above. The enlarged retention holes comprise a space in the final prosthesis base in which manufactured, e.g., denture, teeth may be placed, along with a millable and moldable wax, such that any minor errors or imprecisions in the transferring of the features of the patient's oral cavity and/or the positions of denture teeth to the final prosthesis base can be compensated for, as discussed in more detail below. Moreover, by producing a final prosthesis base from a final-strength, gingiva colored material using a CAD/CAM system, the final prosthesis base does not have to be cast in a conventional manner, and thus, the complicated steps of preparing and finishing the prosthesis base can be reduced. In addition, the issue of bubbles in the cast base that reduce the aesthetics and the stability of the final dental prosthesis can be removed.

In one example embodiment, once the gingiva part, including the enlarged retention holes, of the denture is fabricated in step 120, the retention holes are thereafter filled with a millable and moldable wax, which includes the various waxes generally used by dentists and/or dental lab technicians, in step 122. In step 124, at least a portion of the wax is milled out of each of the retention holes using a milling system or milling machine, such as the one discussed above, in order to mill out the negative part of denture teeth to be placed into the wax-filled retention holes. Thereafter, in step 126, denture teeth are mounted in the negative form that has been milled out of the wax-filled retention holes in the gingiva base. These denture teeth can be manufactured by milling or grinding the denture teeth from a ceramic or metallic block, or another type of similar material capable of use as a denture tooth. Alternatively, the denture teeth can be pre-manufactured teeth, such as those available from VITA or Heraeus, as discussed above. After mounting of the denture teeth into the wax-filled retention holes, a "try-in" denture has now been prepared. This "try-in" denture is now ready to be sent to a dentist in step 128 for an initial fitting with the dental patient.

In step 130, the dental patient will visit the dentist for a second time for this initial fitting with the "try-in" denture. The "try-in" denture is highly realistic, which allows for more accuracy in adapting the denture for the patient's mouth. In particular, the "try-in" denture already includes the final prosthesis base that has been milled from a final strength, gingiva colored material. Moreover, due to the retention holes being filled with a millable and moldable wax, the denture teeth of the "try-in" denture can be easily adjusted to fit the specific features of the patient's oral cavity. Accordingly, in step 132, the dentist will place the "try-in" denture in the patient's mouth, and any adjustments necessary to the denture teeth, such as their positioning and/or location, may be manually made by the dentist to adjust the bite and to fit the patient's specific needs. Because the wax included within the retention holes is moldable, the positions and/or locations of the denture teeth mounted within the wax of the retention holes can be easily, manually shifted or adjusted by the dentist. Once any and/or all adjustments have been made to the denture teeth of the "try-in" denture, the adjusted "try-in" denture is returned to the lab, in step 134, to complete the dental prosthesis.

To complete the dental prosthesis, the enlarged retention holes on the gingiva base are filled-in with a final gum material and the positioning of the dental teeth is set to ensure that the dental prosthesis, as adjusted above, accurately fits with the specific features of the patient's oral cavity and/or bite. In one example embodiment, this process begins at step 136 in which a silicon helper structure 410 (see, e.g., FIG. 4) is created and attached to the denture teeth, to secure the relative position of the adjusted denture teeth 420 with respect to the other denture teeth, as well as the relative position of the adjusted denture teeth with respect to the patient's jaw and/or the gingiva part 201. Thereafter, in step 138, the denture teeth 420 are removed from the retention holes 203 of the "try-in" denture 200 and mounted in the silicon helper structure 410 created in step 136. The removing and mounting of the denture teeth 420 from the "try-in" denture to the silicon helper structure 410 preserves any adjustments that were made by the dentist to the denture teeth. Accordingly, the silicon helper structure 410 will allow for the mounted denture teeth 420 to maintain their adjustments as the prosthesis base is readied for its final curing. Any wax 400 remaining within the retention holes 203 is then removed at step 140, in order to prepare the prosthesis base for the final curing. Alternatively, the silicon helper structure 410 may be attached and positioned over the denture teeth, and any wax 400 remaining within the retention holes 203 may be removed using various tools, without removing the denture teeth 420 from the retention holes 203 and mounting the teeth into the silicon helper structure 410.

Figure 4:
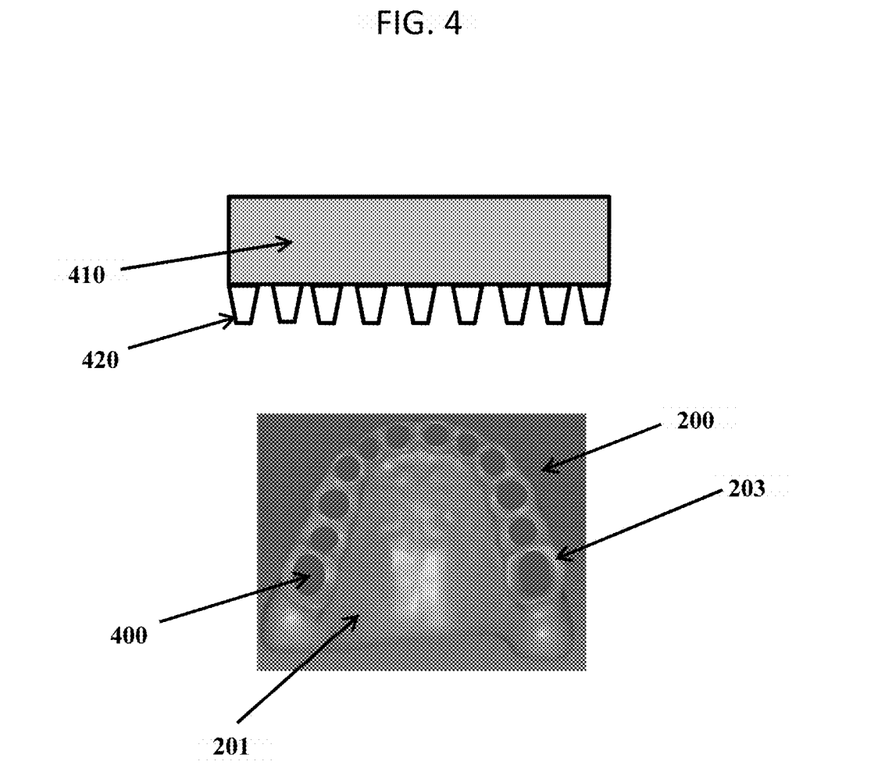
FIG. 4 is a diagram of an example holding device and dental prosthesis configured in accordance with an example embodiment herein.

Once the remaining wax 400 is removed from the retention holes 203, the silicon helper structure 410 with (or without) the mounted denture teeth 420 is positioned over the enlarged retention holes 203 and gingiva part 201 of the denture in step 142. The adjusted denture teeth should be placed within the retention holes and the retention holes are then filled with a liquid gingiva or gum material in step 144, to begin the process of setting the adjusted denture teeth in the final prosthesis base. In step 146, the technician must then let the liquid gum material cure or harden to ensure that the adjusted denture teeth are effectively positioned and set within the final prosthesis base. Once the liquid gum material has cured and the adjusted denture teeth are set, the silicon helper structure 410 may be removed. The final set denture is thereafter polished and individualized for the dental patient in step 148. In one example embodiment, the final denture is individualized by manually painting over any visible transitions between the prosthesis base and the filled and cured retention holes to achieve acceptable aesthetics. For example, the visible transitions may be painted to match the gingiva colored material of the fabricated gingiva part. Thereafter, the dental prosthesis or denture is complete and may be sent back to the dentist at step 150 for the final fitting onto the patient.

Figure 3:
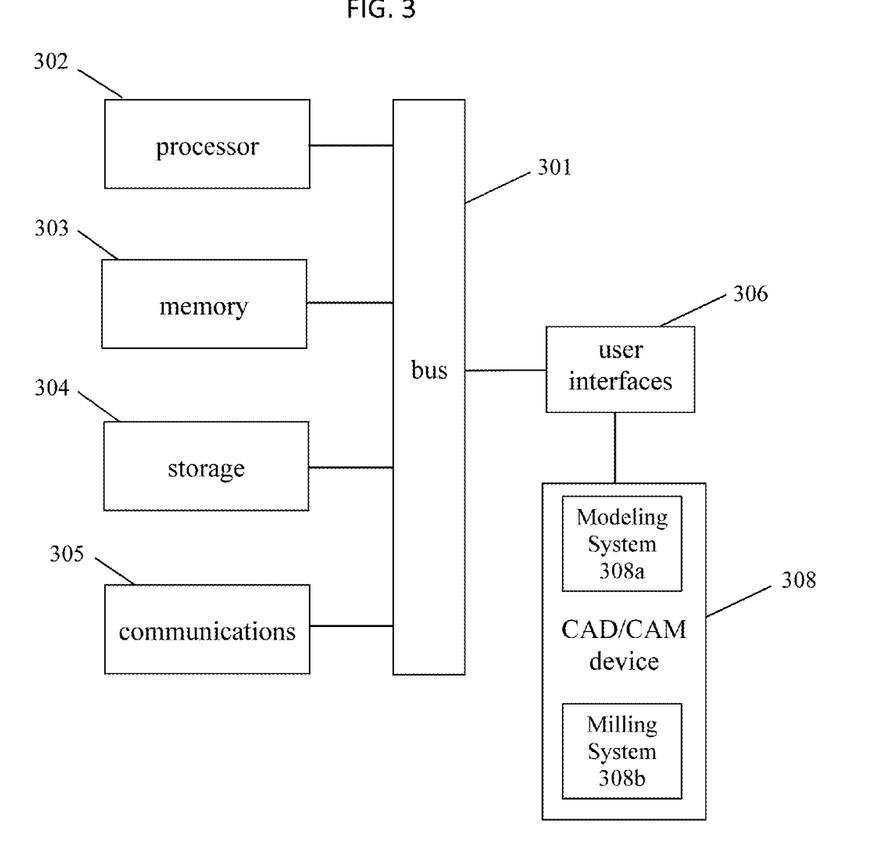
FIG. 3 is an architecture diagram of an example computer system or device which can be used in the practice of example embodiments herein.

FIG. 3 is a diagram of an example computer system. The system, in one example embodiment, may form at least part of the CAD/CAM system used in preparing the dental prosthesis of the present invention, and may be configured to perform one or more steps of the procedure illustrated in FIGS. 1A-1C. The system of FIG. 3 includes a processor 302, a memory 303, a storage device 304, a communications device 305, user interfaces 306, and a CAD/CAM device 308, all of which are coupled to a bus 301.

Processor 302 communicates with the other components of the computer system through bus 301. Storage device 304 includes one or more computer-readable media. Storage device 304 is configured to read and write data including program instructions that may be executed by processor 302 and operating systems (e.g., a general-purpose operating system, such as Microsoft Windows and UNIX, or a custom operating system) that allow processor 302 to control the operation of the other components. Communications device 305 is configured to allow processor 302 to communicate with, for example, a network and the internet. User interfaces 306 can include input devices (e.g., keyboards, mice, joysticks, trackpads, stylus tablets, microphones, and cameras), output devices (e.g., video displays, printers, and speakers), and input/output devices (e.g., touch screens). User interfaces 306 can form at least part of any of the devices, components, and/or systems discussed herein. The CAD/CAM device 308 includes a modeling system 308a configured to perform the digital designing of the gingiva part, with the enlarged retention holes, and the denture teeth, as discussed above. The CAD/CAM device 308 further includes a milling system 308b configured to perform the fabricating of the digitally designed gingiva part that includes the enlarged retention holes, as also discussed above. In one embodiment, the gingiva part is fabricated by the milling system 308b out of a final-strength prosthesis base material that is preferably made of a gingiva colored material. The CAD/CAM device 308 can form at least part of any of the devices, components, and/or systems discussed herein.

Processor 302 is configured to perform part (or all) of any of the procedures described herein. For example, one or more steps of the procedure illustrated in FIGS. 1A-1C can be stored on a non-transitory storage device 304 in the form of computer-readable program instructions. To execute a procedure, the processor loads the appropriate instructions, as stored on storage device 304, into memory 303, and then executes the loaded instructions.

In the foregoing description, example aspects of the invention are described with reference to several example embodiments. Accordingly, the specification should be regarded as illustrative, rather than restrictive. Similarly, the figures illustrated in the drawings, which highlight the functionality and advantages of the invention, are presented for example purposes only. The architecture of the present invention is sufficiently flexible and configurable, such that it may be utilized (and navigated) in ways other than those shown in the accompanying figures.

Software embodiments of example aspects of the invention may be provided as a sequence of instructions, or software, which may be stored on an article of manufacture, e.g., a computer-readable medium having instructions. The instructions on the computer-readable medium may be used to program a computer system or other electronic device. The computer-readable medium may include, but is not limited to, floppy diskettes, optical disks, CD-ROMs, and magneto-optical disks or other types of media suitable for storing electronic instructions.

The techniques described herein, when performed using a computer system, are not limited to any particular software configuration. They may find applicability in any computing or processing environment. The terms "computer-readable medium" and "memory" refer to any medium that is capable of storing, encoding, or transmitting a sequence of instructions for execution by a computer system and that causes the computer system to perform any technique described herein. Furthermore, it is common in the art to speak of software, in one form or another (e.g., program, procedure, process, application, logic, and so on) as taking an action or causing a result. Such expressions are merely a shorthand way of stating that the execution of the software by a computer system causes the processor to perform an action to produce a result. In other embodiments, functions performed by software can instead be performed by hardcoded modules, and thus the invention is not limited only for use with stored software programs. In addition, it is not necessary that procedures described herein be performed with a computer system, and instead they can be performed, in whole or in part, by a human operator.

Although example aspects of the invention have been described in certain specific embodiments, many additional modifications and variations would be apparent to those skilled in the art. It thus should be understood that this invention may be practiced in ways other than those specifically described. Thus, the present example embodiments, again, should be considered in all respects as illustrative and not restrictive.

What is claimed is:

1. A method for preparing a dental prosthesis, the method comprising:
   generating a digital model of an oral cavity;
   generating a digital design of the dental prosthesis that includes a gingiva part and a plurality of manufactured teeth based on the digital model of the oral cavity, wherein the gingiva part includes a plurality of retention holes for seating the plurality of manufactured teeth, respectively;
   digitally enlarging the plurality of retention holes, wherein a size and geometry of each enlarged retention hole is determined based on a size and geometry of a corresponding manufactured tooth for the retention hole; and
   fabricating the gingiva part of the dental prosthesis out of a final strength, gingiva colored base to create a fabricated gingiva part, wherein the fabricated gingiva part includes the enlarged plurality of retention holes.

2. The method according to claim 1, further comprising: filling the enlarged plurality of retention holes with a wax.

3. The method according to claim 2, further comprising: removing respective wax portions from the enlarged plurality of retention holes, each removed portion comprising a negative part of a corresponding manufactured tooth to be seated in the retention hole.

4. The method according to claim 3, further comprising: mounting the plurality of manufactured teeth to the enlarged plurality of retention holes, respectively; and adjusting a position of at least one of the plurality of manufactured teeth relative to a corresponding enlarged retention hole.

5. The method according to claim 4, further comprising: attaching a helper structure to the position-adjusted manufactured teeth so as to preserve a positioning thereof relative to the gingiva part; and
removing any wax remaining within each of the enlarged plurality of retention holes.

6. The method according to claim 5, further comprising: filling each of the enlarged plurality of retention holes with a liquid gingiva material; and
curing the liquid gingiva material.

7. The method according to claim 6, further comprising: painting the cured liquid gingiva material to match the gingiva colored base of the fabricated gingiva part.

8. The method according to claim 1, wherein the generating of the digital design of the dental prosthesis is performed by a computer-aided design (CAD) system, and the fabricating of the gingiva part of the dental prosthesis is performed using a computer-assisted manufacturing (CAM) milling system.

9. The method of claim 1, wherein the digital model of the oral cavity is generated from a digital impression of the oral cavity.

10. The method of claim 1, wherein the digital model of the oral cavity is generated from an extraoral scan of a stone model, the stone model having been created from a physical impression of the oral cavity.

11. The method of claim 1, wherein the plurality of manufactured teeth included in the digital design are representations of premanufactured teeth.

12. The method of claim 1, wherein the plurality of manufactured teeth included in the digital design are computer-generated teeth.

13. The method of claim 1, wherein the plurality of manufactured teeth included in the digital design are biogeneric teeth.

14. The method of claim 1, wherein the generating of the digital design of the dental prosthesis includes (i) automatically selecting the plurality of manufactured teeth from among a plurality of premanufactured teeth and biogeneric teeth, and (ii) automatically determining the relative positioning of the plurality of manufactured teeth within the gingiva part of the dental prosthesis.

15. The method of claim 1, further comprising:
receiving an instruction to modify a location, position, or size of an enlarged retention hole from a user.

16. The method of claim 1, further comprising:
increasing or decreasing an outer margin of an enlarged retention hole of the enlarged plurality of retention holes in accordance with a user instruction.

17. The method of claim 1, wherein the fabricating of the gingiva part of the dental prosthesis is by an additive process.

18. The method of claim 1, wherein the fabricating of the gingiva part of the dental prosthesis is by a subtractive process.

19. A system for preparing a dental prosthesis, comprising:
a processor constructed to:
generate a digital model of an oral cavity,
generate a digital design of the dental prosthesis that includes a gingiva part and a plurality of manufactured teeth based on the digital model of the oral cavity, wherein the gingiva part includes a plurality of retention holes for seating the plurality of manufactured teeth, respectively, and
enlarge the plurality of retention holes, wherein a size and geometry of each enlarged retention hole is determined based on a size and geometry of a corresponding manufactured tooth for the retention hole.

20. The system according to claim 19, wherein the processor is included in a dental computer-aided design/computer-assisted manufacturing (CAD/CAM) device.

21. The system according to claim 19, further comprising:
a milling system constructed to fabricate the gingiva part out of a final strength, gingiva colored base based on the digital design, the gingiva part including the enlarged plurality of retention holes.

22. The system according to claim 19, wherein the processor is further constructed to adjust at least one of a size, a position, and a location of a retention hole of the enlarged plurality of retention holes.

23. The system according to claim 22, wherein the processor is further constructed to adjust the at least one of the size, the position, and the location of the retention hole based on stored information that includes at least one of (i) a measurement related to an adjacent tooth, (ii) a measurement related to sizing of an inner boundary of the retention hole, and (iii) a measurement related to sizing of an outer boundary of the retention hole.

24. The system of claim 19, wherein the processor is further constructed to generate the digital model of the oral cavity from a digital impression of the oral cavity.

25. The system of claim 19, wherein the processor is further constructed to generate the digital model of the oral cavity from an extraoral scan of a stone model, the stone model having been created from a physical impression of the oral cavity.

26. The system of claim 19, further comprising:
a memory constructed to store specifications and geometries respectively corresponding to a plurality of premanufactured teeth,
wherein the plurality of manufactured teeth included in the digital design are representations of the plurality of premanufactured teeth.

27. The system of claim 19, further comprising:
a memory constructed to store information on a plurality of biogeneric teeth, and
wherein the plurality of manufactured teeth included in the digital design correspond to biogeneric teeth whose information is stored in the memory.

28. The system of claim 19, wherein the processor is further constructed to generate the digital design of the dental prosthesis by (i) automatically selecting the plurality of manufactured teeth from among a plurality of premanufactured teeth and biogeneric teeth, and (ii) automatically determining the relative positioning of the plurality of manufactured teeth within the gingiva part of the dental prosthesis.

29. The system of claim 19, wherein the processor is constructed to receive an instruction to modify a location, position, or size of an enlarged retention hole from a user.

30. The system of claim 19, wherein the processor is constructed to increase or decrease an outer margin of an enlarged retention hole of the enlarged plurality of retention holes in accordance with a user instruction.

31. A non-transitory computer-readable medium storing sequences of instructions, the sequences of instructions including instructions which, when executed by a computer system, cause the computer system to:
generate a digital model of an oral cavity,
generate a digital design of the dental prosthesis that includes a gingiva part and a plurality of manufactured teeth based on the digital model of the oral cavity, wherein the gingiva part includes a plurality of retention holes for seating the plurality of manufactured teeth, respectively, and
enlarge the plurality of retention holes, wherein a size and geometry of each enlarged retention hole is determined based on a size and geometry of a corresponding manufactured tooth for the retention hole.

32. The non-transitory computer-readable medium according to claim 31, wherein the instructions, when executed by the computer system, further cause the computer system to:
control fabrication of the gingiva part of the dental prosthesis based on the digital design, the fabricated gingiva part including the enlarged plurality of retention holes.

33. The non-transitory computer-readable medium according to claim 31, wherein the instructions, when executed by the computer system, further cause the computer system to adjust at least one of a size, a position, and a location of a retention hole of the enlarged plurality of retention holes.

34. The non-transitory computer-readable medium according to claim 33, wherein the at least one of the size, the position, and the location of the retention hole is adjusted based on stored information that includes at least one of (i) a measurement related to an adjacent tooth, (ii) a measurement related to sizing of an inner boundary of the retention hole, and (iii) a measurement related to sizing of an outer boundary of the retention hole.

* * * * *